United States Patent [19]

Covey et al.

[11] Patent Number: 5,049,554
[45] Date of Patent: Sep. 17, 1991

[54] PHOSPHOROUS SUBSTITUTED TETRAZOLINONES AND INSECTICIDAL USE THEREOF

[75] Inventors: Rupert A. Covey, Bethany; Richard C. Moore, Wallingford, both of Conn.

[73] Assignee: Uniroyal Chemical Company, Inc., Middlebury, Conn.

[21] Appl. No.: 572,330

[22] Filed: Aug. 21, 1990

Related U.S. Application Data

[63] Continuation of Ser. No. 304,385, Jan. 30, 1989, abandoned, which is a continuation of Ser. No. 16,314, Feb. 19, 1987, abandoned, which is a continuation-in-part of Ser. No. 655,477, Sep. 27, 1984, abandoned, which is a continuation-in-part of Ser. No. 552,573, Nov. 15, 1983, abandoned.

[51] Int. Cl.$^5$ .................... C07F 9/652; A01N 57/08
[52] U.S. Cl. ........................................ 514/92; 548/112
[58] Field of Search ..................... 514/92; 548/112

[56] References Cited

U.S. PATENT DOCUMENTS 3,780,053 12/1973 Miesel ........................ 260/308 C
3,973,010 8/1976 Dawes et al. ................ 424/200
4,211,703 7/1980 Berges ........................ 260/308 P

FOREIGN PATENT DOCUMENTS 932388 7/1963 United Kingdom .

OTHER PUBLICATIONS

Tsuge et al., J. Org. Chem. 45, 5130 (1980).
Horowitz et al., J. Am. Chem. Soc. 81, 3076 (1959).
Vandensavel et al., J. Org. Chem. 88, 675 (1973).

Primary Examiner—David B. Springer
Attorney, Agent, or Firm—Glenn E. Karta

[57] ABSTRACT

Compounds of the formula:

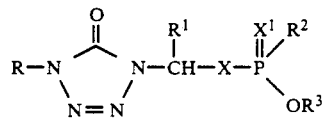

wherein R is alkyl, cycloalkyl, alkoxyalkyl, alkylthioalkyl, haloalkyl, phenyl, naphthyl, alkenyl, substituted phenyl, benzyl or substituted benzyl; $R^1$ is hydrogen, alkyl or phenyl; $R^2$ is alkyl, alkoxy, alkylthio, alkylamino or dialkylamino; $R^3$ is alkyl; and X and $X^1$ are each independently sulfur or oxygen; exhibit insecticidal, acaricidal and nematicidal activity. Also disclosed are compositions comprising such compounds as well as methods of controlling insects, acarids and nematodes.

22 Claims, No Drawings

PHOSPHOROUS SUBSTITUTED TETRAZOLINONES AND INSECTICIDAL USE THEREOF

This is a continuation of application Ser. No. 304,385 filed Jan. 30, 1989, which was a continuation of application Ser. No. 016,314 filed Feb. 19, 1987, which was a continuation-in-part of application Ser. No. 655,477 filed Sep. 27, 1984, which was a continuation-in-part of application Ser. No. 552,573 filed Nov. 16, 1983, all now abandoned.

FIELD OF THE INVENTION

This invention is directed to novel organophosphorous-substituted tetrazolinones, which compounds exhibit unexpectedly desirable activity as insecticides, including as soil-applied insecticides, and as acaricides and nematicides. In other aspects, this invention is directed to pesticidal compositions comprising such compounds as well as to methods of controlling insects, acarids and nematodes employing such compositions.

BACKGROUND OF THE INVENTION

The destruction by nematodes (especially by so-called root-knot nematodes), acarids and insects presents a serious problem to agriculture. A wide variety of field crops are in need of protection from nematodes, acarids and/or insects including such valuable crops as soybeans, corn, peanuts, cotton, alfalfa and tobacco. In addition, vegetables, such as tomatoes, potatoes, sugarbeet, carrots and the like as well as fruits, nuts, ornamentals and seed bed crops such as apples, peaches, peas, citrus fruit and grapes may also require protection from the ravages of such pests.

One particularly difficult type of insect to control are those which, at one or more stages of their life, inhabit the soil and cause destruction to the roots of agriculturally valuable plants. Representative of this type of insect is the corn rootworm.

Corn rootworms are the larvae of several species of beetles of the genus Diabrotica. These larvae cause severe damage to the roots of corn plants, particularly in fields where one corn crop follows another in successive seasons. The adult beetles lay their eggs in the soil of a maturing corn crop The eggs lay dormant in the soil until the following spring. Then they hatch in response to favorable soil temperatures and the larvae feed on the roots of young corn plants causing reduction in yield and/or the stalks to topple over when subjected to either wind or wet soil conditions. The fallen stalks cannot be satisfactorily harvested by mechanical harvesters causing significant losses.

Control of such soil-dwelling insects and nematodes is difficult in that most organophosphorous-type insecticidal and nematicidal compounds have an undesirably short residual life in soil. Accordingly, it is completely unexpected that the novel organophosphorous-substituted tetrazolinone compounds of this invention exhibit desirable foliar insecticidal and acaricidal properties coupled with admirable control of soil-dwelling insects and nematodes.

U.S. Pat. No. 3,780,053 to Miesel shows a class of 5-oxo(thioxo)-1,3-(alkyl, alkenyl or cycloalkyl)-1,2,4-triazolin-4-yl methyl phosphorous derivatives having insecticidal, acaricidal and antihelminthic activity.

Japanese Patent No 1982-14929 to Matsui et al shows certain phosphorothiomethyl-substituted triazolinones which exhibit insecticidal and acaricidal activity.

U.S. Pat. No. 3,973,010 to Dawes et al shows a class of triazolyl phosphoric esters having insecticidal and acaricidal activity.

U.S. Pat. No. 4,211,703 to Berges shows certain phosphoroalkyl and esterified phosphoroalkyl substituted tetrazole thioazoles useful as intermediates in the preparation of certain antibiotics.

European Patent 65,216 to Kubel et al shows certain 5-(1,2,4-triazol-5-ylmethyl)(di)thiophosphonate derivatives having insecticidal, acaricidal, nematicidal and fungicidal activity.

German Offenlegungsschrift 25 27 676 shows a class of 5-triazolylmethyl thiophosph(on)ates useful as insecticides, acaricides and nematicides.

British Patent 932,388 to Sherlock shows certain heterocyclic thiophosphoric acid esters exhibiting acaricidal activity.

Tsuge et al, J. Org. Chem. 45, 5130 (1980); Horwitz et al, J. Am. Chem. Soc. 81, 3076 (1959); and Vandensavel et al, J. Org Chem , 88, 675 (1973) all show processes for the production of tetrazolinones.

However, while certain of the above-listed publications disclose pesticidally active compounds, it would nevertheless be desirable to possess compounds which exhibited enhanced control of pests, particularly of soil-dwelling insects.

Accordingly, it is an object of this invention to provide novel compounds, exhibiting unexpectedly desirable pesticidal activity.

It is a further object of this invention to provide novel compounds exhibiting admirable activity against soil dwelling insects.

It is another object of this invention to provide pesticidal compositions comprising such novel compounds.

It is yet another object of this invention to provide methods of controlling pests employing such compositions.

The above objects, and the additional objects, will become more fully apparent from the following disclosure and accompanying Examples.

DESCRIPTION OF THE INVENTION

In one aspect, the present claimed invention is directed to a compound having the formula:

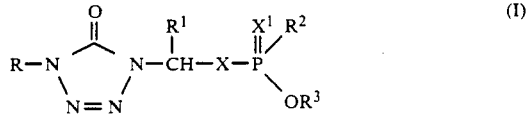

wherein:
R is selected from the group consisting of:
  $C_1$–$C_{12}$ alkyl;
  $C_5$–$C_6$ cycloalkyl;
  $C_2$–$C_{13}$ alkoxyalkyl;
  $C_2$–$C_6$ alkylthioalkyl;
  $C_1$–$C_6$ haloalkyl (wherein halogen is chlorine, fluorine, bromine or iodine);
  phenyl;
  naphthyl;
  $C_3$–$C_{12}$ alkenyl;
  phenyl substituted with at least one member of the group consisting of:

halogen (i.e., fluorine, chlorine, bromine or iodine),
$C_1$-$C_4$ alkyl,
$C_1$-$C_4$ alkoxy,
$C_1$-$C_4$ alkylthio,
trihalomethyl (wherein halogen is fluorine, chlorine, bromine or iodine),
trihalomethoxy (wherein halogen is fluorine, chlorine, bromine or iodine),
$C_2$-$C_5$ alkoxycarbonyl,
nitro,
cyano,
carboxy,
methylenedioxy,
phenoxy, and
phenoxy substituted with halogen (i.e., chlorine, fluorine, bromine or iodine), $C_1$-$C_4$ alkyl or $C_1$-$C_4$ alkoxy;
benzyl; and
benzyl substituted with at least one member of the group consisting of:
halogen (i.e., fluorine, chlorine, bromine or iodine),
$C_1$-$C_4$ alkyl,
$C_1$-$C_4$ alkoxy,
methylenedioxy,
$C_2$-$C_5$ alkoxycarbonyl,
phenoxy,
nitro,
cyano,
trihalomethyl (wherein halogen is fluorine, chlorine, bromine or iodine),
trihalomethoxy (wherein halogen is fluorine, chlorine, bromine or iodine), and
phenoxy substituted with halogen (i.e., fluorine, chlorine, bromine or iodine), $C_1$-$C_4$ alkyl or $C_1$-$C_4$ alkoxy;
$R^1$ is hydrogen;
$C_1$-$C_4$ alkyl: or
phenyl;
$R^2$ is $C_1$-$C_5$ alkyl;
$C_1$-$C_5$ alkoxy;
$C_1$-$C_5$ alkylthio;
$C_1$-$C_5$ alkylamino; or
$C_2$-$C_{10}$ dialkylamino;
$R^3$ is $C_1$-$C_5$ alkyl; and
X and $X^1$ are the same or different and are oxygen or sulfur.
Preferably:
X is sulfur;
R is $C_1$-$C_8$ alkyl,
benzyl,
phenyl,
allyl,
phenyl,
phenyl substituted with at least one member selected from the group consisting of:
fluorine,
chlorine,
bromine,
$C_1$-$C_4$ alkyl,
$C_1$-$C_3$ alkoxy,
phenoxy,
nitro,
cyano,
trihalomethyl,
methylthio,
trichloromethylthio, and
phenoxy substituted with chlorine, fluorine, bromine, $C_1$-$C_3$ alkyl, ethoxy or methoxy; or
benzyl substituted with at least one member selected from the group consisting of:
$C_1$-$C_2$ alkyl,
fluorine,
chlorine,
bromine,
$C_1$-$C_2$ alkoxy,
trifluoromethyl,
methylenedioxy,
nitro, and
cyano;
$R^2$ is $C_1$-$C_3$ alkyl;
$C_1$-$C_3$ alkylthio; or
$C_1$-$C_3$ alkoxy; and
$R^3$ is $C_1$-$C_4$ alkyl.
More preferably:
R is $C_1$-$C_4$ alkyl,
benzyl,
phenyl, or
phenyl substituted with fluorine, chlorine, methyl, methoxy, nitro, cyano or trifluoromethyl;
$R^1$ is hydrogen or methyl;
$R^2$ is methoxy,
ethoxy,
methylthio, or
ethylthio;
$R^3$ is methyl or ethyl; and
$X^1$ and $X^2$ are sulfur.
Particularly preferred compounds include
O,O-dimethyl S-[1-phenyl-5(4H)-tetrazolinone-4-methyl] phosphorodithioate;
O,O-diethyl S-[1-(2-fluoro)phenyl-5(4H)-tetrazolinone-4-methyl] phosphorodithioate;
O,O-diethyl S-[1-(2-chloro)phenyl-5(4H)-tetrazolinone-4-methyl] phosphorodithiate;
O,O-diethyl S-[1-t-butyl-5-(4H)-tetrazolinone-4-methyl] phosphorodithioate;
O,O-diethyl S-[1-phenyl-5(4H)-tetrazolinone-4-methyl] phosphorodithioate;
O,O-diethyl S-[1-phenyl-5(4H)-tetrazolinone-4-(1-ethyl)] phosphorodithioate;
O,O-diethyl S-[1-benzyl-5(4H)-tetrazolinone-4-methyl] phosphorodithioate;
O,O-diethyl S-[1-(4-fluoro)phenyl-5(4H)-tetrazolinone-4-methyl] phosphorodithioate;
O,O-diethyl S-[1-methyl-5(4H)-tetrazolinone-4-methyl] phosphorodithioate;
O,O-diethyl S-[1-ethyl-5(4H)-tetrazolinone-4-methyl] phosphorodithioate;
O-ethyl,S-n-propyl S-[1-methyl-5(4H)-tetrazolinone-4-methyl] phosphoroylthioate;
O-ethyl,S-n-propyl S-[1-ethyl-5(4H)-tetrazolinone-4-methyl] phosphoroylthioate;
O-ethyl,S-n-propyl S-[1-n-propyl-5(4H)-tetrazolinone-4-methyl] phosphoroylthioate;
O-ethyl,S-n-propyl S-[1-t-butyl-5(4H)-tetrazolinone-4-methyl] phosphoroylthioate;
O-ethyl,S-n-propyl S-[1-i-propyl-5(4H)-tetrazolinone-4-methyl] phosphoroylthioate;
O-ethyl,S-n-propyl S-[1-phenyl-5(4H)-tetrazolinone-4-methyl] phosphoroylthioate; and
O-ethyl,S-n-propyl S-[1-allyl-5(4H)-tetrazolinone-4-methyl] phosphoroylthioate.

The compounds of this invention may be prepared by reacting a chloromethyltetrazolinone of the formula:

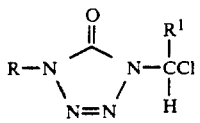

wherein R and R¹ are as defined for Formula (I) above, with an alkali metal or ammonium phosphate salt of the formula:

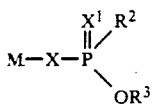

wherein X, X¹, R² and R³ are as defined above and wherein M is an alkali metal or ammonium cation.

Typically, the chloromethyltetrazolinone and phosphate salt are employed in about equivalent amounts, although up to a 50% excess of phosphate salt is frequently utilized. This reaction may be carried out at between about −20° C. and about 100° C. with temperatures between about 20° C. and about 50° C. being preferred. Generally, a solvent inert to the reactants is used. Suitable solvents for the reaction are ethers, such as diethylether, diisopropylether, dioxane, dimethoxyethane and tetrahydrofuran; amides, such as N,N-dialkylated carboxamides; aliphatic, aromatic and halogenated hydrocarbons such as hexane, benzene, toluene, xylene, methylene chloride, chloroform, carbon tetrachloride, and chlorobenzene; nitriles such as acetonitrile; dimethylsulfoxide; ketones, such as acetone and methylethylketone; and alcohols such as methyl and ethyl alcohol.

The phosphate salts employed as starting materials are well known compounds which ar commercially available.

The chloromethyltetrazolinone starting materials can be produced by reacting the appropriate 1-substituted-5(4H)-tetrazolinone with an appropriate aldehyde and thionyl chloride. The aldehyde and tetrazolinone are generally employed in about equivalent amounts with up to one equivalent excess of aldehyde typically being utilized. At least one equivalent and up to one equivalent excess of thionyl chloride should be employed. In any case, an amount of thionyl chloride at least equivalent to the amount of aldehyde should be used, and preferably in a 10% molar excess. Such reaction may be carried out at between about 0° and about 130° C., preferably at between about 70° and about 120° C. Generally, a solvent inert to the reactants is used. Suitable solvents for the reaction are ethers, such as diethylether, diisopropylether, dioxane, dimethoxyethane and tetrahydrofuran; amides, such as N,N-dialkylated carboxamides; aliphatic, aromatic and halogenated hydrocarbons, such as hexane, benzene, toluene, xylene, methylene chloride, chloroform, carbon tetrachloride, and chlorobenzene; nitriles, such as acetonitrile; and dimethylsulfoxide.

Appropriate 1-substituted-5(4H)-tetralinones can be prepared by processes such as those described by Horwitz et al, J. Am. Chem. Soc. 81, 3076 (1959) and by Tsuge et al, J. Org. Chem. 45, 5130 (1980), which processes involve (in general) reacting an appropriate azide with an appropriate isocyanate, which azides and isocyanates are both commercially available chemicals.

The composition of this invention is comprised of (A) a compound having a structure within that of Formula (I) above and (B) a suitable carrier. Such suitable carriers may be solid or liquid in nature.

Suitable liquid carriers may be comprised of water, alcohols, ketones, phenols, toluene and xylenes. In such formulations, additives conventionally employed in the art may be utilized such as, for example, one or more surface active agents and/or inert diluents, to facilitate handling an application of the resulting pesticide composition.

The pesticidal compositions may alternatively comprise solid carriers taking the form of dusts, granules, wettable powders, pastes, aerosols, emulsions, emulsifiable concentrates, and water-soluble solids.

For example, the pesticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applicable directly to the loci to be treated. Alternatively, the powdered solid carrier containing the compound admixed therewith may be dispersed in water to form a suspension for application in such form.

Granular formulations of the compounds, suitable for application by broadcasting, side dressing, soil incorporation or seed treatment, are suitably prepared using a granular or pellitized form of carrier such as granular clays, vermiculite, charcoal or corn cobs.

Alternatively, the pesticidal compounds may be applied in liquids or sprays when utilized in a liquid carrier, such as in a solution comprising a compatible solvent such as acetone, benzene, toluene or kerosene, or as dispersed in a suitable non-solvent medium, for example, water.

Another method of application to loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which may be non-ionic, cationic or anionic. Suitable surface-active agents include those known in the art, such as those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. Concentration per unit area, where plants constitute the loci of treatment, may range between about 0.01 and about 50 pounds per acre, with concentrations of between about 0.1 and about 10 pounds per acre preferably being employed for crops such as corn, tobacco, rice and the like.

To combat pests, sprays of the compounds may be applied to the pests directly and/or to plants upon which they feed or nest. The pesticidally active formulations may also be applied to the soil o other medium in which the pests are present.

Harmful insects, nematodes and acarids attack a wide variety of plants, including both ornamental and agricultural plants and inflict damage by consuming root and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will, of course, vary depending upon such circumstances as geographic area, climate, topography, plant tolerance, etc. For specific circumstances, one skilled in the art may readily determine the proper compound, concentration and method of application by routine experimentation.

The compounds of the invention are particularly useful as insecticides, nematodes and acaricides, for foliar and/or soil application. The compounds are particularly effective for controlling insects, such as corn rootworm, which live in the soil during one or more phases of their lives, by means of soil application.

EXAMPLES

The following Examples are intended to further illustrate the invention, and are not intended to limit the scope of the invention in any manner whatsoever.

EXAMPLE 1

Preparation of 4-chloromethyl-l-phenyl-5(4H)-tetrazolinone

A mixture of 7.7 grams (0.0475 mole) of 1-phenyl-5(4H)-tetrazolinone, 2.1 grams (0.07 mole) of paraformaldehyde and 5.8 ml (9.5 grams, 0.08 mole) of thionyl chloride in 40 ml of toluene was heated to 75°–80° C., whereupon evolution of HCl took place. Heating was continued for another 1.25 hours, during which time the temperature rose to 110° C. The solution was decanted and the remaining solid was washed with a small amount of toluene. The toluene solutions were combined and concentrated under reduced pressure. The last traces of solvent were removed by warming to 40° C. at 0.2 mm Hg pressure, to yield 10.43 grams of a yellow oil. This oil was taken up in ether and the solution filtered. The filtrate was concentrated under reduced pressure and finally warmed to 40° C. at 0.15 mm Hg pressure. The resulting product (9.7 grams; 97% of theoretical) was a thick yellow oil. The infrared (IR) spectrum indicated carboxyl absorption at 1740 cm$^{-1}$ (rather than 1710 cm$^{-1}$ for the starting material). Nuclear magnetic resonance (NMR) analysis showed a sharp singlet at 5.6 ppm.

EXAMPLE 2

Preparation of 4-(1-chloroethyl)-l-phenyl-5(4H)-tetrazolinone

To a suspension of 2.5 grams (0.015 mole) of 1-phenyl-5(4H)-tetrazolinone in 15 ml of toluene were added 1.4 ml (1.1 grams, 0.025 mole) of acetaldehyde and 2.0 ml (3.3 grams, 0.028 mole) of thionyl chloride. The mixture was heated to 70°–75° C., at which temperature hydrogen chloride gas was evolved. Heating was continued for 1.5 hours at 80°–85° C. The HCl evolution subsided during this time, and most of the solid dissolved. The mixture was filtered and the filtrate evaporated to dryness. The oil was taken up in diethyl ether, the solution filtered and the solvent removed from the filtrate. A total of 3.15 grams, 93% of theoretical, was obtained. The structure was confirmed by the IR and NMR analyses.

EXAMPLE 3

Preparation of O,O-Diethyl S-[1-phenyl-5(4H)-tetrazolinone-4-methyl] phosphorodithioate (Compound No. 1)

To 2.4 grams (0.0114 mole) of 4-chloromethyl-1-phenyl-5(4H)-tetrazolinone (of Example 1) in 25 ml of acetonitrile were added 3.7 grams (0.0182 mole) of ammonium O,O-diethyldithiophosphate, and the mixture was warmed to 40°–50° C. for two hours, during which time a white precipitate was formed. This was removed by filtration, and the filtrate was evaporated to dryness. Toluene was added, and the mixture was extracted three times with 15 ml portions in water. The toluene solution was dried with anhydrous magnesium sulfate and concentrated on a rotary evaporator. The residue was then stripped of solvent at 49° (0.15 mm Hg) giving 3.49 grams (85% yield) of a yellow oil which was identified as the product by IR and NMR analyses.

EXAMPLE 4

Preparation of O,O-Diethyl S-[1-phenyl-5(4H)-tetrazolinone-4-(1-ethyl)] phosphorodithioate (Compound No. 2)

4-(1-chloroethyl)-l-phenyl-5(4H)-tetrazolinone (of Example 2) (3.0 grams, 0.013 mole) and 2.8 grams (0.014 mole) of ammonium O,O-diethyl-dithiophosphate were combined in 25 ml of acetonitrile, and the mixture was heated for 1 hour at 40°–45° C. and then stirred for 2 hours at room temperature. The reaction mixture was filtered and the filtrate evaporated to dryness. The residual oil was taken up in toluene, the solution filtered in order to remove some insoluble solid, and the filtrate was washed three times with 15 ml portions of water. The toluene solution was dried over anhydrous magnesium sulfate, and the solvent was removed at 40° C. and 0.15 mm Hg pressure to yield 3.15 grams (64% of theoretical) of a yellow oil. The structure was confirmed by IR and NMR analyses.

EXAMPLE 5

Compounds No. 3–49

Additional compounds were prepared applying essentially the experimental approach previously described. The compounds were analyzed for determination of their key structural configuration and functional groups. The analytical determinations were substantially confirmed by nuclear magnetic resonance and infrared methods. These compounds and their NMR spectra are listed in Table I. In such table; s=singlet; d=doublet; t=triplet; q=quartet; and m=multiplet.

TABLE I

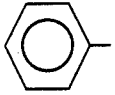

| Cmpd. No. | R | $R^1$ | $R^2$ | $R^3$ | X | $X^1$ | NMR $\delta$ CDCl$_3$ (60MHz) |
|---|---|---|---|---|---|---|---|
| 1 | 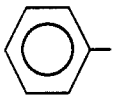 | H | OC$_2$H$_5$ | C$_2$H$_5$ | S | S | 1.35(t, 6H), 4.17(m, 4H), 5.27, 5.55(2s, 2H), 7.40(m, 3H), 7.87(m, 2H) |
| 2 | 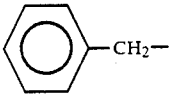 | CH$_3$ | OC$_2$H$_5$ | C$_2$H$_5$ | S | S | 1.26(t, 3H), 1.37(t, 3H), 1.96(d, 3H), 3.80–4.48(m, 4H), 5.5–6.2(m, 1H), 7.1–7.6 (m, 3H), 7.7–8.0(m, 2H) |
| 3 | n-C$_8$H$_{17}$ | H | OC$_2$H$_5$ | C$_2$H$_5$ | S | S | 0.8–2.3(m, 21H), 3.8–4.5(m, 6H), 5.17, 5.46(2s, 2H) |
| 4 | 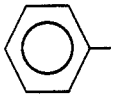 | H | OC$_2$H$_5$ | C$_2$H$_5$ | S | S | 1.39(t, 6H), 4.22(m, 4H), 5.05(s, 2H), 5.13, 5.43(2s, 2H), 7.34(s, 5H) |
| 5 | 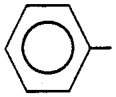 | H | OCH$_3$ | CH$_3$ | S | S | * |
| 6 |  | 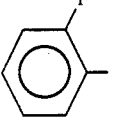 | OC$_2$H$_5$ | C$_2$H$_5$ | S | S | 1.30(m, 6H), 3.72–4.52(m, 4H), 6.69, 6.87(2s, 1H), 7.18–7.72(m, 8H), 7.79–8.03(m, 2H) |
| 7 | 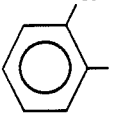 | H | OC$_2$H$_5$ | C$_2$H$_5$ | S | S | 1.37(t, 6H), 4.20(m, 4H), 5.26, 5.55(2s, 2H), 7.40(m, 4H) |
| 8 | 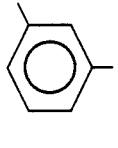 | H | OC$_2$H$_5$ | C$_2$H$_5$ | S | S | 1.36(t, 6H), 4.22(m, 4H), 5.27, 5.56(2s, 2H), 7.45(m, 4H) |
| 9 | 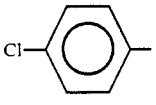 | H | OC$_2$H$_5$ | C$_2$H$_5$ | S | S | 1.37(t, 6H), 4.29(m, 4H), 5.30, 5.59(2s, 2H), 7.55(m, 4H) |
| 10 | 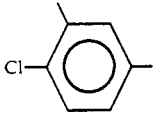 | H | OC$_2$H$_5$ | C$_2$H$_5$ | S | S | 1.32(t, 6H), 4.10(m, 4H), 5.20, 5.49(2s, 2H), 7.57(m, 4H) |
| 11 |  | H | OC$_2$H$_5$ | C$_2$H$_5$ | S | S | 1.36(t, 6H), 4.22(m, 4H), 5.27, 5.57(2s, 2H), 7.58(m, 3H) |

TABLE I-continued
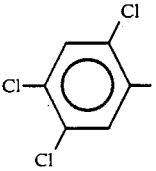
| Cmpd. No. | R | R$^1$ | R$^2$ | R$^3$ | X | X$^1$ | NMR δ CDCl$_3$ (60MHz) |
|---|---|---|---|---|---|---|---|
| 12 | 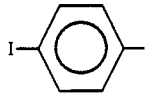 | H | OC$_2$H$_5$ | C$_2$H$_5$ | S | S | 1.36(t, 6H), 4.19(m, 4H), 5.24, 5.54(2s, 2H), 7.60(d, 2H) |
| 13 | 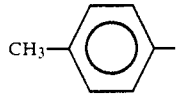 | H | OC$_2$H$_5$ | C$_2$H$_5$ | S | S | 1.35(t, 6H), 4.20(m, 4H), 5.24, 5.54(2s, 2H), 7.75(s, 4H) |
| 14 | 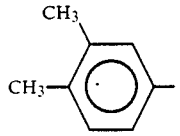 | H | OC$_2$H$_5$ | C$_2$H$_5$ | S | S | 1.33(t, 6H), 2.36(s, 3H), 4.18(m, 4H), 5.25, 5.53(2s, 2H), 7.54(q, 4H) |
| 15 | 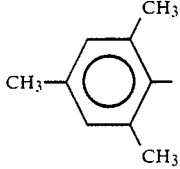 | H | OC$_2$H$_5$ | C$_2$H$_5$ | S | S | 1.36(t, 6H), 2.31(s, 6H), 4.23(m, 4H), 5.26, 5.56(2s, 2H), 7.33(m, 4H) |
| 16 | 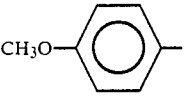 | H | OC$_2$H$_5$ | C$_2$H$_5$ | S | S | 1.37(t, 6H), 2.09(s, 6H), 2.31(s, 3H), 4.19(m, 4H), 5.27, 5.56(2s, 2H), 6.96(s, 2H) |
| 17 | 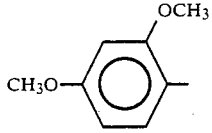 | H | OC$_2$H$_5$ | C$_2$H$_5$ | S | S | 1.34(t, 6H), 3.79(s, 3H), 4.21(m, 4H), 5.25, 5.54(2s, 2H), 7.39(q, 4H) |
| 18 | 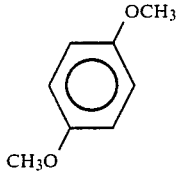 | H | OC$_2$H$_5$ | C$_2$H$_5$ | S | S | 1.38(t, 6H), 3.78(s, 6H), 4.22(m, 4H), 5.23, 5.50(2s, 2H), 6.98(m, 2H) |
| 19 | 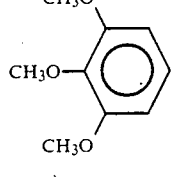 | H | OC$_2$H$_5$ | C$_2$H$_5$ | S | S | 1.33(t, 6H), 3.73(s, 3H), 3.79(s, 3H), 4.16(m, 4H), 5.19, 5.46(2s, 2H), 6.53(m, 2H), 7.11(m, 1H) |
| 20 |  | H | OC$_2$H$_5$ | C$_2$H$_5$ | S | S | 1.37(t, 6H), 3.86(s, 3H), 3.89(s, 6H), 4.22(m, 4H), 5.26, 5.55(2s, 2H), 7.18(s, 2H) |

TABLE I-continued

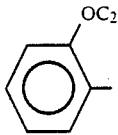

| Cmpd. No. | R | R¹ | R² | R³ | X | X¹ | NMR δ CDCl₃ (60MHz) |
|---|---|---|---|---|---|---|---|
| 21 | 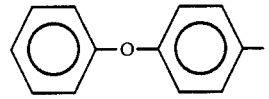 (2-OC₂H₅-phenyl) | H | OC₂H₅ | C₂H₅ | S | S | 1.35(t, 9H), 4.25(m, 6H), 5.22, 5.51(2s, 2H), 6.90–7.60(m, 4H) |
| 22 | 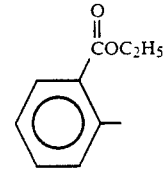 (phenoxyphenyl) | H | OC₂H₅ | C₂H₅ | S | S | 1.37(t, 6H), 4.20(m, 4H), 5.26, 5.55(2s, 2H), 6.88–8.00(m, 9H) |
| 23 |  (2-COC₂H₅-phenyl) | H | OC₂H₅ | C₂H₅ | S | S | 1.35(m, 9H), 3.18(m, 6H), 5.21, 5.50(2s, 2H), 7.55(m, 3H), 8.00(m, 1H) |
| 24 |  (phenyl) | H | O-i-C₃H₇ | i-C₃H₇ | S | S | 1.28(d, 6H), 1.38(d, 6H), 4.87(m, 2H), 5.30, 5.60(2s, 2H), 7.22–7.68(m, 3H), 7.78–8.10(m, 2H) |
| 25 | 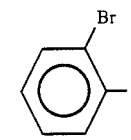 (phenyl) | H | O-n-C₄H₉ | n-C₄H₉ | S | S | 0.90(t, 6H), 1.15–1.98(m, 8H), 4.10(m, 4H), 5.24, 5.54(2s, 2H), 7.10–7.67(m, 3H), 7.70–8.10(m, 2H) |
| 26 | 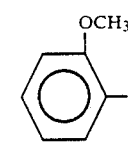 (2-Br-phenyl) | H | OC₂H₅ | C₂H₅ | S | S | 1.32(t, 6H), 3.77(s, 3H), 4.22(m, 4H), 5.21, 5.50(2s, 2H), 7.12(m, 2H), 7.27(m, 2H) |
| 27 | 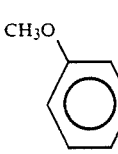 (2-OCH₃-phenyl) | H | OC₂H₅ | C₂H₅ | S | S | 1.32(t, 6H), 3.77(s, 3H), 4.22(m, 4H), 5.21, 5.50(2s, 2H), 7.12(m, 2H), 7.27(m, 2H) |
| 28 | 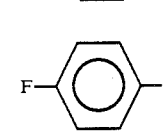 (3-OCH₃-phenyl) | H | OC₂H₅ | C₂H₅ | S | S | 1.32(t, 6H), 3.76(s, 3H), 4.15(m, 4H), 5.18, 5.47(2s, 2H), 6.78(m, 1H), 7.38(m, 3H) |
| 29 | 4-F-phenyl | H | OC₂H₅ | C₂H₅ | S | S | 1.35(t, 6H), 4.2(m, 4H), 5.25, 5.55(2s, 2H), 7.14(m, 2H), 7.8(m, 2H) |
| 30 | CH₃ | H | OC₂H₅ | C₂H₅ | S | S | 1.35(t, 6H), 3.60(s, 3H), 4.13(m, 4H), 5.14, 5.43(2s, 2H) |
| 31 | C₂H₅ | H | OC₂H₅ | C₂H₅ | S | S | 1.35(m, 9H), 3.93(m, 6H), 5.00, 5.28(2s, 2H) |
| 32 | n-C₃H₇ | H | OC₂H₅ | C₂H₅ | S | S | 0.97(t, 3H), 1.32(t, 6H), 1.75(m, 2H), 3.93(m, 6H), 5.08, 5.35(2s, 2H) |
| 33 | t-C₄H₉ | H | OC₂H₅ | C₂H₅ | S | S | 1.34(t, 6H), 1.62(s, 9H), 4.16(m, 4H), 5.13, 5.42(2s, 2H) |

TABLE I-continued

Structure:
$R-N-N(C=O)-N(CH(R^1)-X-P(=X^1)(R^2)(OR^3))-N=N$ (1,2,3,4-tetrazolinone with CH-X-P side chain)

| Cmpd. No. | R | R¹ | R² | R³ | X | X¹ | NMR δ CDCl₃ (60MHz) |
|---|---|---|---|---|---|---|---|
| 34 | 1-naphthyl | H | OC₂H₅ | C₂H₅ | S | S | 1.31(t, 6H), 4.13(m, 4H), 5.22, 5.51(2s, 2H), 7.2–8.1(m, 7H) |
| 35 | 2-methylphenyl | H | OC₂H₅ | C₂H₅ | S | S | 1.34(t, 6H), 2.25(s, 3H), 4.18(m, 4H), 5.24, 5.53(2s, 2H), 7.23(s, 4H) |
| 36 | 3-methylphenyl | H | OC₂H₅ | C₂H₅ | S | S | 1.36(t, 6H), 2.46(s, 3H), 4.18(m, 4H), 5.25, 5.54(2s, 2H), 7.15–7.80(m, 4H) |
| 37 | CH₃ | H | S-n-C₃H₇ | C₂H₅ | S | O | 1.0(t, 3H), 1.37(t, 3H), 1.77(m, 2H), 2.92(m, 2H), 3.59(s, 3H), 4.29(m, 2H), 5.19, 5.46(2s, 2H) |
| 38 | C₂H₅ | H | S-n-C₃H₇ | C₂H₅ | S | O | 0.90–1.70(m, 9H), 1.85(m, 2H), 2.90(m, 2H), 3.8–4.5(m, 4H), 5.26, 5.53(2s, 2H) |
| 39 | n-C₃H₇ | H | S-n-C₃H₇ | C₂H₅ | S | O | 0.75–2.20(m, 13H), 2.85(m, 2H), 3.75–4.5(m, 4H), 5.21, 5.47(2s, 2H) |
| 40 | t-C₄H₉ | H | S-n-C₃H₇ | C₂H₅ | S | O | 0.80–1.55(m, 8H), 1.62(s, 9H), 2.60–3.25(m, 2H), 3.78–4.45(m, 2H), 5.18, 5.44(2s, 2H) |
| 41 | i-C₃H₇ | H | S-n-C₃H₇ | C₂H₅ | S | O | 0.75–2.25(m, 14H), 2.87(m, 2H), 4.28(m, 3H), 5.19, 5.46(2s, 2H) |
| 42 | thian-2-yl (6-membered S ring) | H | S-n-C₃H₇ | C₂H₅ | S | O | 0.70–2.25(m, 18H), 2.83(m, 2H), 4.15(m, 3H), 5.19, 5.45(2s, 2H) |
| 43 | cyclohexyl | H | S-n-C₃H₇ | C₂H₅ | S | O | 0.5–2.1(m, 8H), 2.88(m, 2H), 4.18(m, 2H), 5.27, 5.54(2s, 2H), 7.39(m, 3H), 7.87(m, 2H) |
| 44 | H₂C=CH—CH₂ | H | S-n-C₃H₇ | C₂H₅ | S | O | 0.56–2.2(m, 8H), 2.85(m, 2H), 4.23(m, 2H), 4.54(d, 2H), 5.0–5.6(m, 4H), 5.5–6.3(m, 1H) |
| 45 | n-C₄H₉ | H | S-n-C₃H₇ | C₂H₅ | S | O | 0.55–2.15(m, 15H), 2.95(m, 2H), 3.60–4.62(m, 4H), 5.23, 5.50(2s, 2H) |
| 46 | CH₃ | H | OC₂H₅ | C₂H₅ | O | S | 1.32(m, 6H), 4.12(m, 4H), 5.62, 5.72(2s, 2H), 3.59(s, 3H) |
| 47 | C₂H₅ | H | OC₂H₅ | C₂H₅ | O | S | 1.35(m, 9H), 4.07(m, 6H), 5.61, 5.80(2s, 2H) |
| 48 | n-C₃H₇ | H | OC₂H₅ | C₂H₅ | O | S | 0.95(t, 3H), 1.36(m, 6H), 1.90(m, 2H), 3.98(m, 6H), 5.68, 5.76(2s, 2H) |

TABLE I-continued

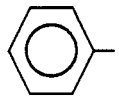

| Cmpd. No. | R | R¹ | R² | R³ | X | X¹ | NMR δ $CDCl_3$ (60MHz) |
|---|---|---|---|---|---|---|---|
| 49 | (phenyl) | H | $OC_2H_5$ | $C_2H_5$ | O | S | 1.28(t, 6H), 4.13(m, 4H), 5.70, 5.40(2s, 2H), 7.34(m, 3H), 7.75(m, 2H) |

*mixture of isomers

Employing processes essentially similar to those described in the above Examples, the following compounds are prepared.

TABLE II

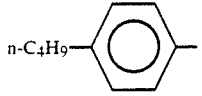

| Cmpd. No. | R | R¹ | R² | R³ | X | X¹ |
|---|---|---|---|---|---|---|
| 50 | $CH_3$ | H | $NHC_2H_5$ | $C_2H_5$ | S | O |
| 51 | n-$C_4H_9$-(phenyl)- | H | $OC_2H_5$ | $C_2H_5$ | S | S |
| 52 | 3-$OCH_3$,4-$NO_2$-(phenyl)- | H | $OC_2H_5$ | $C_2H_5$ | S | S |
| 53 | 2-CN-(phenyl)- | H | $OC_2H_5$ | $C_2H_5$ | S | S |
| 54 | n-$C_4H_9O$-(phenyl)- | H | $OC_2H_5$ | $C_2H_5$ | S | S |
| 55 | (phenyl)- | n-$C_4H_9$ | $OC_2H_5$ | $C_2H_5$ | S | S |
| 56 | (phenyl)- | H | $NHC_2H_5$ | $C_2H_5$ | S | S |
| 57 | $ClCH_2$-$CH_2$-(phenyl)-$CH_2$-(phenyl)- |  | $OC_2H_5$ | $C_2H_5$ | S | S |

TABLE II-continued $$R-N \overset{\overset{O}{\|}}{\underset{N=N}{-}} N-CH(R^1)-X-\overset{\overset{X^1}{\|}}{P}(R^2)(OR^3)$$

| Cmpd. No. | R | R¹ | R² | R³ | X | X¹ |
|---|---|---|---|---|---|---|
| 58 | 3,4-(CH₃O)₂C₆H₃CH₂— | H | OC₂H₅ | C₂H₅ | S | S |
| 59 | 3-CN-C₆H₄CH₂— | CH₃ | OC₂H₅ | C₂H₅ | S | S |
| 60 | CH₃ | H | S-n-C₃H₇ | C₂H₅ | S | O |
| 61 | CH₃ | H | S-s-C₄H₉ | C₂H₅ | S | O |
| 62 | CH₃ | H | S-t-C₄H₉ | C₂H₅ | S | O |
| 63 | CH₃ | H | CH₃ | C₂H₅ | S | O |
| 64 | CH₃ | H | C₂H₅ | C₂H₅ | S | O |
| 65 | CH₃ | H | n-C₃H₇ | C₂H₅ | O | S |
| 66 | CH₃ | CH₃ | s-C₄H₉ | CH₃ | O | S |
| 67 | CH₃ | C₆H₅ | t-C₄H₉ | C₂H₅ | S | O |
| 68 | CH₃ | H | C₂H₅ | C₂H₅ | S | S |
| 69 | C₂H₅ | H | C₂H₅ | C₂H₅ | S | S |
| 70 | i-C₃H₇ | H | C₂H₅ | C₂H₅ | S | S |
| 71 | t-C₄H₉ | H | C₂H₅ | C₂H₅ | S | S |
| 72 | C₆H₅ | H | C₂H₅ | C₂H₅ | S | S |
| 73 | 2-Cl-C₆H₄ | H | C₂H₅ | i-C₃H₇ | O | O |
| 74 | C₆H₅CH₂— | H | C₂H₅ | CH₃ | O | O |
| 75 | 2-CH₃-C₆H₄CH₂— | H | C₂H₅ | n-C₄H₉ | O | S |
| 76 | CH₃ | H | SCH₃ | C₂H₅ | O | S |
| 77 | CH₃ | H | NHCH₃ | C₂H₅ | S | S |
| 78 | CH₃ | H | NH-s-C₄H₉ | C₂H₅ | S | O |
| 79 | CH₃ | H | N(CH₃)₂ | C₂H₅ | O | S |
| 80 | CH₃ | H | N(C₂H₅)₂ | C₂H₅ | O | O |

EXAMPLE 6

Control of Tobacco Budworm

A mixture was prepared of 0.6 gram of compound No. 1, 10 ml acetone, four drops of a surfactant (Tween 20 [trademark]; ethoxylate sorbitan monolaurate) and water (ca. 90 ml) resulting in a solution wherein said compound was present at a concentration of 6000 parts per million (ppm). To five plastic cells were added about 5 grams of wheat germ/soyflower diet and the diet was impregnated with 0.2 ml of the above solution. Additional cells (five each) were prepared containing said diet and 0.2 ml of a 1,000 ppm solution of said compound, respectively, and into each cell a tobacco budworm larvae was placed. After six days, the cells were inspected and percent control was noted with the following results:

| Concentration, ppm | 6,000 | 1,000 |
|---|---|---|
| Control, % | 80 | 37 |

The data indicate that the compound (No. 1) of Example 3 is effective against tobacco budworm.

EXAMPLE 7

Control of Corn Rootworm

A solution was prepared as described in Example 6 containing Compound No. 1 at a 6,000 ppm concentration. Said solution was further diluted resulting in various concentrations of active ingredient as indicated in the Table below. Two corn seedlings were first soaked for one hour in a flask containing the solution having a certain concentration of active ingredient, and the seedling is transferred to a plastic bag containing a paper towel which had been treated with 5 ml of the respective same concentration 18 hours after the bag had been closed, five 3rd instar corn rootworm larvae were placed in each bag, and after six days, the effectiveness of the compound on the corn rootworm larvae was determined. The results are listed below.

| Concentration, ppm | 1,000 | 500 | 100 | 50 | 20 |
|---|---|---|---|---|---|
| Control, % | 100 | 100 | 100 | 78 | 78 |

It will be noted that compound No. 1 is a very effective insecticide for the control of corn rootworm.

EXAMPLE 8

Control of Mites

Following essentially the procedures of the previous examples, a solution was prepared containing Compound No. 1 at a 1000 ppm concentration. Two 10-day old cow pea plants were sprayed to run-off with that solution and then they were left to dry for one day. Thereafter, 25 mites were placed on each of two leaves per plant, the mites' area of movement being restricted by a circle of sticky material (Tanglefoot [trademark]). After five days, the effect of the chemical on the mites was observed to be 100% control.

EXAMPLE 9

Control of Rice Planthopper

Two 10-day old rice plants were treated in similar fashion as described in Example 8 except the rice plants were placed under a plastic hood, and ten adult planthoppers were placed on each plant. The concentrations of active material (Compound No. 1) and percent pest control are indicated below:

| Concentration, ppm | 1,000 | 500 |
|---|---|---|
| Control, % | 100 | 89 |

EXAMPLE 10

Control of Tobacco Budworm, Corn Rootworm, Mites and Rice Planthopper by Compounds 2-49

Following the testing procedures outlined above, additional compounds of this invention were evaluated. The results are summarized in Table III. It should be noted that the percent control values were obtained at pesticide concentration of 1000 ppm for testing of mites, rice planthoppers and corn rootworms; and at 3000 ppm for tobacco budworms; except otherwise indicated. Also, the abbreviated column headings have these meanings:

MI mites;
RPH: rice planthopper;
TBW: tobacco budworm;
CR: corn rootworm.

TABLE III

| | Percent Control of Mites and Insects | | | |
|---|---|---|---|---|
| Cpd. No. | MI | RPH | TBW | CR |
| 1 | 100 | 100 | 37[3] | 100 |
| 2 | 90 | 100 | 60[1] | 100 |
| 3 | 0 | 94[2] | 0[3] | 100[2] |
| 4 | 95 | 100 | 80 | 100 |
| 5 | 0 | 60 | 20 | 100 |
| 6 | 90 | 64[2] | 20[1] | 100 |
| 7 | 80 | 100[2] | 0[3] | 100[2] |
| 8 | 0 | 100[2] | 0[3] | 100[2] |
| 9 | 80 | 95 | 20[3] | 69 |
| 10 | 0 | 80 | 80[3] | 100 |
| 11 | 0 | 80 | 80 | 29 |
| 12 | 0 | 70 | 100 | 50[4] |
| 13 | 80 | 60 | 20[3] | 38 |
| 14 | 0 | 100 | 20 | 100 |
| 15 | 0 | 70 | 20 | 56 |
| 16 | 0 | 90 | 33 | 50[4] |
| 17 | 0 | 70 | 40 | 43 |
| 18 | 0 | — | 0[3] | 62 |
| 19 | 0 | 40 | 0[3] | 100[2] |
| 20 | 0 | 70 | 56 | 50[4] |
| 21 | 0 | 100[2] | 0[3] | 100[2] |
| 22 | 30 | 70 | 53 | 62 |
| 23 | 90 | 100[2] | 0[3] | 100[2] |
| 24 | 0 | 95 | 0 | 33[4] |
| 25 | 0 | 0 | 60 | 33[4] |
| 26 | 20 | 70 | 60 | 80[4] |
| 27 | 70 | 70 | 0 | 20[4] |
| 28 | 50 | 100 | 0 | 40[4] |
| 29 | 80 | 100 | 100 | 80[4] |
| 30 | 95 | 100 | 0 | 100[4] |
| 31 | 90 | 100 | 0 | 100[4] |
| 32 | 90 | 0 | 0 | 100[4] |
| 33 | 80 | 60 | 20 | 100[4] |
| 34 | 0 | 0 | 0 | 43[4] |
| 35 | 60 | 95 | 20 | 100[4] |
| 36 | 0 | 100 | 0 | 100[4] |
| 37 | 100 | 95 | 100 | 100[4] |
| 38 | 100 | 100 | 100 | 100[4] |
| 39 | 95 | 100 | 80 | 100[4] |
| 40 | 50 | 100 | 100 | 100[4] |
| 41 | 100 | 95 | 100 | 100[4] |
| 42 | 98 | 90 | 60 | 100[4] |
| 43 | 100 | 95 | 100 | 100[4] |
| 44 | 98 | 100 | 60 | 100[4] |
| 45 | 50 | 95 | 60 | 100[4] |
| 46 | 70 | 90 | 0 | 100[4] |
| 47 | 0 | 50 | 0 | 100[4] |
| 48 | 0 | 50 | 0 | 100[4] |
| 49 | 80 | 0 | 0 | 100[4] |

Remarks:
[1] at 6,000 ppm
[2] at 5,000 ppm
[3] at 1,000 ppm
[4] at 500 ppm

The results demonstrate the usefulness of the chemicals of this invention for combatting mites and insects.

Similar results are obtained when employing the compounds listed in Table II.

EXAMPLE 11

Nematode Soil Test

The Southern root-knot nematode, *Meloidogyne incognita*, was reared in sandy culture soil using tomato as a host plant. Roots from culture plants were ground in a Waring blender. Ground roots and culture soil were mixed with equal parts of uninfested soil and the mixture was placed in pots. Test formulations were prepared at 1000 ppm. Twenty-five ml of the dilution was drenched per pot, giving a resultant soil concentration of 50 ppm. One day after treatment, two tomato seedlings were planted in each pot. Twelve days after planting, soil was washed from roots and treatments were evaluated by comparing the number of knots on plants roots from treated soil to those from the untreated nematode-infested control. The results are shown in Table IV.

TABLE IV

| Compound Number | % Control of Nematodes 50 PPM Soil Concentration |
|---|---|
| 2 | 85 |
| 5 | 50 |
| 30 | 90 |
| 32 | 90 |
| 33 | 70 |
| 35 | 60 |
| 37 | 100 |
| 38 | 100 |
| 39 | 100 |
| 40 | 95 |
| 41 | 100 |
| 42 | 100 |
| 43 | 100 |
| 44 | 95 |
| 45 | 100 |
| 49 | 50 |

EXAMPLE 12

Southern Corn Rootworm Soil Test

In this example, test formulations of several representative compounds of the invention were prepared as follows:

Prior to treatment, two hybrid corn seed were planted in the soil. Test chemicals were prepared as a 40 ppm suspension in water. Four pots, containing 270 grams of soil each, were drenched with 40 ml of the suspension to give a resulting soil concentration of 4 ppm. One week after treatment, ten Southern corn rootworm larvae were placed in each pot. Two weeks after treatment, pots were emptied and the roots washed free of soil. All surviving larvae were collected from the water and percent control was calculated. The results are shown in Table V.

TABLE V

| Compound Number | % Control of Corn Rootworm 4 PPM Soil Concentration |
|---|---|
| 1 | 97 |
| 2 | 82 |
| 5 | 11 |
| 9 | 78 |
| 10 | 26 |
| 30 | 97 |
| 33 | 89 |
| 37 | 45 |
| 38 | 42 |
| 39 | 9 |
| 40 | 47 |
| 41 | 38 |
| 42 | 27 |
| 43 | 29 |
| 44 | 24 |
| 45 | 78 |

What is claimed is:

1. A compound having the formula:

$$R-N\underset{N=N}{\overset{\displaystyle\diagup}{\diagdown}}\overset{\displaystyle\overset{O}{\|}}{C}-N-\underset{R^1}{\overset{}{\text{C}}}H-X-\overset{X^1}{\underset{\|}{P}}\diagdown_{OR^3}^{R^2} \quad (I)$$

wherein:
R is selected from the group consisting of:
  $C_1$–$C_{12}$ alkyl;
  $C_5$–$C_6$ cycloalkyl;
  $C_2$–$C_{13}$ alkoxyalkyl;
  $C_2$–$C_6$ alkylthioalkyl;
  $C_1$–$C_6$ haloalkyl;
  phenyl;
  naphthyl;
  $C_3$–$C_{12}$ alkenyl;
  phenyl substituted with at least one member of the group consisting of:
    halogen,
    $C_1$–$C_4$ alkyl,
    $C_1$–$C_4$ alkoxy,
    $C_1$–$C_4$ alkylthio,
    trihalomethyl,
    trihalomethoxy,
    $C_2$–$C_5$ alkoxycarbonyl,
    nitro,
    cyano,
    carboxy,
    methylenedioxy,
    phenoxy, and
    phenoxy substituted with chlorine, fluorine, bromine, iodine, $C_1$–$C_4$ alkyl or $C_1$–$C_4$ alkoxy;
  benzyl; and
  benzyl substituted with at least one member of the group consisting of:
    halogen,
    $C_1$–$C_4$ alkyl,
    $C_1$–$C_4$ alkoxy,
    methylenedioxy,
    $C_2$–$C_5$ alkoxycarbonyl,
    phenoxy,
    nitro,
    cyano,
    trihalomethyl,
    trihalomethoxy,
    phenoxy substituted with fluorine, chlorine, bromine, iodine, $C_1$–$C_4$ alkyl or $C_1$–$C_4$ alkoxy;
$R^1$ is hydrogen;
  $C_1$–$C_4$ alkyl; or
  phenyl;
$R^2$ is $C_1$–$C_5$ alkyl;
  $C_1$–$C_5$ alkoxy;
  $C_1$–$C_5$ alkylthio;
  $C_1$–$C_5$ alkylamino; or $C_2$-$C_{10}$ dialkylamino;
$R^3$ is $C_1$-$C_5$ alkyl; and
X and $X^1$ are the same or different and are oxygen or sulfur.

2. A compound in accordance with claim 1 wherein:
X is sulfur;
R is $C_1$-$C_8$ alkyl,
benzyl,
phenyl,
allyl,
phenyl,
phenyl substituted with at least one member selected from the group consisting of:
  fluorine,
  chlorine,
  bromine,
  $C_1$-$C_4$ alkyl,
  $C_1$-$C_3$ alkoxy,
  phenoxy,
  nitro,
  cyano,
  trihalomethyl,
  methylthio,
  trichloromethylthio, and
  phenoxy substituted with chlorine, fluorine, bromine, $C_1$-$C_3$ alkyl, ethoxy or methoxy; or
benzyl substituted with at least one member selected from the group consisting of:
  $C_1$-$C_2$ alkyl,
  fluorine,
  chlorine,
  bromine,
  $C_1$-$C_2$ alkoxy,
  trifluoromethyl,
  methylenedioxy,
  nitro, and
  cyano;
$R^2$ is $C_1$-$C_3$ alkyl;
  $C_1$-$C_3$ alkylthio; or
  $C_1$-$C_3$ alkoxy; and
$R^3$ is $C_1$-$C_4$ alkyl.

3. A compound in accordance with claim 2 wherein:
R is $C_1$-$C_4$ alkyl,
benzyl,
phenyl, or
phenyl substituted with fluorine, chlorine, methyl, methoxy, nitro, cyano or trifluoromethyl;
$R^1$ is hydrogen or methyl;
$R^2$ is methoxy,
  ethoxy,
  methylthio, or
  ethylthio;
$R^3$ is methyl or ethyl; and
$X^1$ and $X^2$ are sulfur.

4. A compound in accordance with claim 1 wherein said compound is selected from the group consisting of:
O,O-dimethyl S-[1-phenyl-5(4H)-tetrazolinone-4-methyl] phosphorodithioate;
O,O-diethyl S-[1-(2-fluoro)phenyl-5(4H)-tetrazolinone-4-methyl] phosphorodithioate;
O,O-diethyl S-[1-(2-chloro)phenyl-5(4H)-tetrazolinone-4-methyl] phosphorodithiate;
O,O-diethyl S-[1-t-butyl-5-(4H)-tetrazolinone-4-methyl] phosphorodithioate;
O,O-diethyl S-[1-phenyl-5(4H)-tetrazolinone-4-methyl] phosphorodithioate;
O,O-diethyl S-[1-phenyl-5(4H)-tetrazolinone-4-(1-ethyl)] phosphorodithioate;
O,O-diethyl S-[1-benzyl-5(4H)-tetrazolinone-4-methyl] phosphorodithioate;
O,O-diethyl S-[1-(4-fluoro)phenyl-5(4H)-tetrazolinone-4-methyl] phosphorodithioate;
O,O-diethyl S-[1-methyl-5(4H)-tetrazolinone-4-methyl] phosphorodithioate;
O,O-diethyl S-[1-ethyl-5(4H)-tetrazolinone-4-methyl] phosphorodithioate;
O-ethyl,S-n-propyl S-!1-methyl-5(4H)-tetrazolinone-4-methyl] phosphoroylthioate;
O-ethyl,S-n-propyl S-[1-ethyl-5(4H)-tetrazolinone-4-methyl] phosphoroylthioate;
O-ethyl,S-n-propyl S-[1-n-propyl-5(4H)-tetrazolinone-4-methyl] phosphoroylthioate;
O-ethyl,S-n-propyl S-[1-t-butyl-5(4H)-tetrazolinone-4-methyl] phosphoroylthioate;
O-ethyl,S-n-propyl S-[1-i-propyl-5(4H)-tetrazolinone-4-methyl] phosphoroylthioate;
O-ethyl,S-n-propyl S-[1-phenyl-5(4H)-tetrazolinone-4-methyl] phosphoroylthioate: and
O-ethyl,S-n-propyl S-!1-allyl-5(4H)-tetrazolinone-4-methyl] phosphoroylthioate.

5. O,O-diethyl, S-[1-methyl-5(4H)-tetrazolinone-4-methyl] phosphorodithioate.

6. A pesticidal composition comprising:
(A) a compound having the formula:

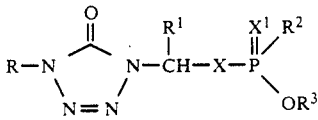

wherein:
R is selected from the group consisting of:
  $C_1$-$C_{12}$ alkyl;
  $C_5$-$C_6$ cycloalkyl;
  $C_2$-$C_{13}$ alkoxyalkyl;
  $C_2$-$C_6$ alkylthioalkyl;
  $C_1$-$C_6$ haloalkyl;
  phenyl;
  naphthyl;
  $C_3$-$C_{12}$ alkenyl;
  phenyl substituted with at least one member of the group consisting of:
  halogen,
  $C_1$-$C_4$ alkyl,
  $C_1$-$C_4$ alkoxy,
  $C_1$-$C_4$ alkylthio,
  trihalomethyl,
  trihalomethoxy,
  $C_2$-$C_5$ alkoxycarbonyl,
  nitro,
  cyano,
  carboxy,
  methylenedioxy,
  phenoxy, and
  phenoxy substituted with chlorine, fluorine, bromine, iodine, $C_1$-$C_4$ alkyl or $C_1$-$C_4$ alkoxy;
benzyl; and
benzyl substituted with at least one member of the group consisting of:
  halogen,
  $C_1$-$C_4$ alkyl,
  $C_1$-$C_4$ alkoxy,
  methylenedioxy,
  $C_2$-$C_5$ alkoxycarbonyl,
  phenoxy, nitro,
cyano,
trihalomethyl,
trihalomethoxy,
phenoxy substituted with fluorine, chlorine, bromine, iodine, $C_1$-$C_4$ alkyl or $C_1$-$C_4$ alkoxy;

$R^1$ is hydrogen;
$C_1$-$C_4$ alkyl; or
phenyl;

$R^2$ is $C_1$-$C_5$ alkyl;
$C_1$-$C_5$ alkoxy;
$C_1$-$C_5$ alkylthio;
$C_1$-$C_5$ alkylamino; or
$C_2$-$C_{10}$ dialkylamino;

$R^3$ is $C_1$-$C_5$ alkyl; and
X and $X^1$ are the same or different and are oxygen or sulfur; and (B) a suitable carrier.

7. A composition in accordance with claim 6 wherein, in component (A):

X is sulfur;
R is $C_1$-$C_8$ alkyl,
benzyl,
phenyl,
allyl,
phenyl,
phenyl substituted with at least one member selected from the group consisting of:
fluorine,
chlorine,
bromine,
$C_1$-$C_4$ alkyl,
$C_1$-$C_3$ alkoxy,
phenoxy,
nitro,
cyano,
trihalomethyl,
methylthio,
trichloromethylthio, and
phenoxy substituted with chlorine, fluorine, bromine, $C_1$-$C_3$ alkyl, ethoxy or methoxy; or
benzyl substituted with at least one member selected from the group consisting of:
$C_1$-$C_2$ alkyl,
fluorine,
chlorine,
bromine,
$C_1$-$C_2$ alkoxy,
trifluoromethyl,
methylenedioxy,
nitro, and
cyano;

$R^2$ is $C_1$-$C_3$ alkyl;
$C_1$-$C_3$ alkylthio; or
$C_1$-$C_3$ alkoxy; and $R^3$ is $C_1$-$C_4$ alkyl.

8. A composition within the scope of claim 7 wherein, in component (A):

R is $C_1$-$C_4$ alkyl,
benzyl,
phenyl, or
phenyl substituted with fluorine, chlorine, methyl, methoxy, nitro, cyano or trifluoromethyl;

$R^1$ is hydrogen or methyl;
$R^2$ is methoxy,
ethoxy,
methylthio, or
ethylthio;

$R^3$ is methyl or ethyl; and
$X^1$ and $X^2$ are sulfur.

9. A composition in accordance with claim 6 wherein component (A) is selected from the group consisting of:

O,O-dimethyl S-[1-phenyl-5(4H)-tetrazolinone-4-methyl] phosphorodithioate;
O,O-diethyl S-[1-(2-fluoro)phenyl-5(4H)-tetrazolinone-4-methyl] phosphorodithioate;
O,O-diethyl S-[1-(2-chloro)phenyl-5(4H)-tetrazolinone-4-methyl] phosphorodithiate;
O,O-diethyl S-[1-t-butyl-5-(4H)-tetrazolinone-4-methyl] phosphorodithioate;
O,O-diethyl S-[1-phenyl-5(4H)-tetrazolinone-4-methyl] phosphorodithioate;
O,O-diethyl S-[1-phenyl-5(4H)-tetrazolinone-4-(1-ethyl)] phosphorodithioate;
O,O-diethyl S-[1-benzyl-5(4H)-tetrazolinone-4-methyl] phosphorodithioate;
O,O-diethyl S-[1-(4-fluoro)phenyl-5(4H)-tetrazolinone-4-methyl] phosphorodithioate;
O,O-diethyl S-[1-methyl-5(4H)-tetrazolinone-4-methyl] phosphorodithioate;
O,O-diethyl S-[1-ethyl-5(4H)-tetrazolinone-4-methyl] phosphorodithioate;
O-ethyl,S-n-propyl S-[1-methyl-5(4H)-tetrazolinone-4-methyl] phosphoroylthioate;
O-ethyl,S-n-propyl S-[1-ethyl-5(4H)-tetrazolinone-4-methyl] phosphoroylthioate;
O-ethyl,S-n-propyl S-[1-n-propyl-5(4H)-tetrazolinone-4-methyl] phosphoroylthioate;
O-ethyl,S-n-propyl S-[1-t-butyl-5(4H)-tetrazolinone-4-methyl] phosphoroylthioate;
O-ethyl,S-n-propyl S-[1-i-propyl-5(4H)-tetrazolinone-4-methyl] phosphoroylthioate;
O-ethyl,S-n-propyl S-[1-phenyl-5(4H)-tetrazolinone-4-methyl] phosphoroylthioate; and
O-ethyl,S-n-propyl S-[1-allyl-5(4H)-tetrazolinone-4-methyl] phosphoroylthioate.

10. A composition in accordance with claim 9 wherein component (A) is O,O-diethyl, S-[1-methyl-5(4H)-tetrazolinone-4-methyl] phosphorodithioate.

11. A method of controlling insects comprising the use of an insecticidally effective amount of a compound having the formula:

$$R-N \overset{\underset{\parallel}{O}}{\underset{N=N}{\diagdown}} \overset{R^1}{\underset{\diagup}{N-CH-X-P}} \overset{X^1}{\underset{OR^3}{\diagdown}} \overset{R^2}{} \quad (I)$$

wherein:
R is selected from the group consisting of:
$C_1$-$C_{12}$ alkyl;
$C_5$-$C_6$ cycloalkyl;
$C_2$-$C_{13}$ alkoxyalkyl;
$C_2$-$C_6$ alkylthioalkyl;
$C_1$-$C_6$ haloalkyl;
phenyl;
naphthyl;
$C_3$-$C_{12}$ alkenyl; phenyl substituted with at least one member of the group consisting of:
halogen,
$C_1$-$C_4$ alkyl,
$C_1$-$C_4$ alkoxy,
$C_1$-$C_4$ alkylthio,
trihalomethyl,
trihalomethoxy, $C_2$-$C_5$ alkoxycarbonyl,
nitro,
cyano,
carboxy,
methylenedioxy,
phenoxy, and
phenoxy substituted with chlorine, fluorine, bromine, iodine, $C_1$-$C_4$ alkyl or $C_1$-$C_4$ alkoxy;
benzyl; and
benzyl substituted with at least one member of the group consisting of:
halogen,
$C_1$-$C_4$ alkyl,
$C_1$-$C_4$ alkoxy,
methylenedioxy,
$C_2$-$C_5$ alkoxycarbonyl,
phenoxy,
nitro,
cyano,
trihalomethyl,
trihalomethoxy,
phenoxy substituted with fluorine, chlorine, bromine, iodine, $C_1$-$C_4$ alkyl or $C_1$-$C_4$ alkoxy;
$R^1$ is hydrogen;
$C_1$-$C_4$ alkyl; or
phenyl;
$R^2$ is $C_1$-$C_5$ alkyl;
$C_1$-$C_5$ alkoxy;
$C_1$-$C_5$ alkylthio;
$C_1$-$C_5$ alkylamino; or
$C_2$-$C_{10}$ dialkylamino;
$R^3$ is $C_1$-$C_5$ alkyl; and
X and $X^1$ are the same or different and are oxygen or sulfur.

12. A method in accordance with claim 11 wherein:
X is sulfur;
R is $C_1$-$C_8$ alkyl,
benzyl,
phenyl,
allyl,
phenyl,
phenyl substituted with at least one member selected from the group consisting of:
fluorine,
chlorine,
bromine,
$C_1$-$C_4$ alkyl,
$C_1$-$C_3$ alkoxy,
phenoxy,
nitro,
cyano,
trihalomethyl,
methylthio,
trichloromethylthio, and
phenoxy substituted with chlorine, fluorine, bromine, $C_1$-$C_3$ alkyl, ethoxy or methoxy; or
benzyl substituted with at least one member selected from the group consisting of:
$C_1$-$C_2$ alkyl,
fluorine,
chlorine,
bromine,
$C_1$-$C_2$ alkoxy,
trifluoromethyl,
methylenedioxy,
nitro, and
cyano;
$R^2$ is $C_1$-$C_3$ alkyl;

$C_1$-$C_3$ alkylthio; or
$C_1$-$C_3$ alkoxy; and
$R^3$ is $C_1$-$C_4$ alkyl.

13. A method in accordance with claim 12 wherein:
R is $C_1$-$C_4$ alkyl,
benzyl,
phenyl, or
phenyl substituted with fluorine, chlorine, methyl, methoxy, nitro, cyano or trifluoromethyl;
$R^1$ is hydrogen or methyl;
$R^2$ is methoxy,
ethoxy,
methylthio, or
ethylthio;
$R^3$ is methyl or ethyl; and
$X^1$ and $X^2$ are sulfur.

14. A method in accordance with claim 11 wherein said compound is selected from the group consisting of:
O,O-dimethyl S-[1-phenyl-5(4H)-tetrazolinone-4-methyl] phosphorodithioate;
O,O-diethyl S-[1-(2-fluoro)phenyl-5(4H)-tetrazolinone-4-methyl] phosphorodithioate;
O,O-diethyl S-[1-(2-chloro)phenyl-5(4H)-tetrazolinone-4-methyl] phosphorodithiate;
O,O-diethyl S-[1-t-butyl-5-(4H)-tetrazolinone-4-methyl] phosphorodithioate;
O,O-diethyl S-[1-phenyl-5(4H)-tetrazolinone-4-methyl] phosphorodithioate;
O,O-diethyl S-[1-phenyl-5(4H)-tetrazolinone-4-(1-ethyl)] phosphorodithioate;
O,O-diethyl S-[1-benzyl-5(4H)-tetrazolinone-4-methyl] phosphorodithioate;
O,O-diethyl S-[1-(4-fluoro)phenyl-5(4H)-tetrazolinone-4methyl] phosphorodithioate;
O,O-diethyl S-[1-methyl-5(4H)-tetrazolinone-4-methyl] phosphorodithioate;
O,O-diethyl S-[1-ethyl-5(4H)-tetrazolinone-4-methyl] phosphorodithioate;
O-ethyl,S-n-propyl S-[1-methyl-5(4H)-tetrazolinone-4-methyl] phosphoroylthioate;
O-ethyl,S-n-propyl S-[1-ethyl-5(4H)-tetrazolinone-4-methyl] phosphoroylthioate;
O-ethyl,S-n-propyl S-[1-n-propyl-5(4H)-tetrazolinone-4-methyl] phosphoroylthioate;
O-ethyl,S-n-propyl S-!1-t-butyl-5(4H)-tetrazolinone-4-methyl] phosphoroylthioate;
O-ethyl,S-n-propyl S-[1-i-propyl-5(4H)-tetrazolinone-4-methyl] phosphoroylthioate;
O-ethyl,S-n-propyl S-[1-phenyl-5(4H)-tetrazolinone-4-methyl] phosphoroylthioate; and
O-ethyl,S-n-propyl S-[1-allyl-5(4H)-tetrazolinone-4-methyl] phosphoroylthioate.

15. A method in accordance with claim 11 wherein said compound is O,O-diethyl, S-[1-methyl-5(4H)-tetrazolinone-4-methyl] phosphorodithioate.

16. A method in accordance with claim 11 wherein said compound is applied directly to the soil.

17. A method in accordance with claim 12 wherein said compound is applied directly to the soil.

18. A method in accordance with claim 13 wherein said compound is applied directly to the soil.

19. A method in accordance with claim 14 wherein said compound is applied directly to the soil.

20. A method in accordance with claim 15 wherein said compound is applied directly to the soil.

21. A method of controlling nematodes comprising the use of a nematicidally effective amount of:
(A) a compound having the formula:

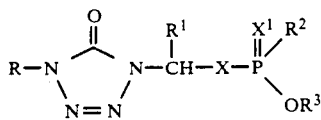

wherein:
R is selected from the group consisting of:
C$_1$–C$_{12}$ alkyl;
C$_5$–C$_6$ cycloalkyl;
C$_2$–C$_{13}$ alkoxyalkyl;
C$_2$–C$_6$ alkylthioalkyl;
C$_1$–C$_6$ haloalkyl;
phenyl;
naphthyl;
C$_3$–C$_{12}$ alkenyl;
phenyl substituted with at least one member of the group consisting of:
halogen,
C$_1$–C$_4$ alkyl,
C$_1$–C$_4$ alkoxy,
C$_1$–C$_4$ alkylthio,
trihalomethyl,
trihalomethoxy,
C$_2$–C$_5$ alkoxycarbonyl,
nitro,
cyano,
carboxy,
methylenedioxy,
phenoxy, and
phenoxy substituted with chlorine, fluorine, bromine, iodine, C$_1$–C$_4$ alkyl or C$_1$–C$_4$ alkoxy;
benzyl; and
benzyl substituted with at least one member of the group consisting of:
halogen,
C$_1$–C$_4$ alkyl,
C$_1$–C$_4$ alkoxy,
methylenedioxy,
C$_2$–C$_5$ alkoxycarbonyl,
phenoxy,
nitro,
cyano,
trihalomethyl,
trihalomethoxy,
phenoxy substituted with fluorine, chlorine, bromine, iodine, C$_1$–C$_4$ alkyl or C$_1$–C$_4$ alkoxy;
R$^1$ is hydrogen;
C$_1$–C$_4$ alkyl; or phenyl;
R$^2$ is C$_1$–C$_5$ alkyl;
C$_1$–C$_5$ alkoxy;
C$_1$–C$_5$ alkylthio;
C$_1$–C$_5$ alkylamino; or
C$_2$–C$_{10}$ dialkylamino;
R$^3$ is C$_1$–C$_5$ alkyl; and
X and X$^1$ are the same or different and are oxygen or sulfur.
22. A method of controlling acarids comprising the use of an acaricidally effective amount of:
(A) a compound having the formula:

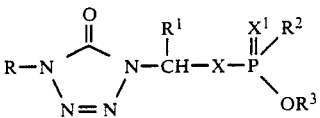

wherein:
R is selected from the group consisting of:
C$_1$–C$_{12}$ alkyl;
C$_5$–C$_6$ cycloalkyl;
C$_2$–C$_{13}$ alkoxyalkyl;
C$_2$–C$_6$ alkylthioalkyl;
C$_1$–C$_6$ haloalkyl;
phenyl;
naphthyl;
C$_3$–C$_{12}$ alkenyl;
phenyl substituted with at least one member of the group consisting of:
halogen,
C$_1$–C$_4$ alkyl,
C$_1$–C$_4$ alkoxy,
C$_1$–C$_4$ alkylthio,
trihalomethyl,
trihalomethoxy,
C$_2$–C$_5$ alkoxycarbonyl,
nitro,
cyano,
carboxy,
methylenedioxy,
phenoxy, and
phenoxy substituted with chlorine, fluorine, bromine, iodine, C$_1$–C$_4$ alkyl or C$_1$–C$_4$ alkoxy;
benzyl; and
benzyl substituted with at least one member of the group consisting of:
halogen,
C$_1$–C$_4$ alkyl,
C$_1$–C$_4$ alkoxy,
methylenedioxy,
C$_2$–C$_5$ alkoxycarbonyl,
phenoxy,
nitro,
cyano,
trihalomethyl,
trihalomethoxy,
phenoxy substituted with fluorine, chlorine, bromine, iodine, C$_1$–C$_4$ alkyl or C$_1$–C$_4$ alkoxy;
R$^1$ is hydrogen;
C$_1$–C$_4$ alkyl; or phenyl;
R$^2$ is C$_1$–C$_5$ alkyl;
C$_1$–C$_5$ alkoxy;
C$_1$–C$_5$ alkylthio;
C$_1$–C$_5$ alkylamino; or
C$_2$–C$_{10}$ dialkylamino;
R$^3$ is C$_1$–C$_5$ alkyl; and
X and X$^1$ are the same or different and are oxygen or sulfur.

* * * * *